(12) United States Patent
Hyland et al.

(10) Patent No.: US 12,384,994 B2
(45) Date of Patent: Aug. 12, 2025

(54) GEL TRAY FOR BACTERIA TRANSFORMATION LAB

(71) Applicant: C.C. Imex, San Diego, CA (US)

(72) Inventors: Callen Elizabeth Hyland, La Jolla, CA (US); Christopher Karl Schroeder, San Diego, CA (US); Rita Mei Yi Wong, San Diego, CA (US); Richard Tat Lee Chan, La Jolla, CA (US)

(73) Assignee: C.C. Imex, San Diego, CA (US)

( * ) Notice: Subject to any disclaimer, the term of this patent is extended or adjusted under 35 U.S.C. 154(b) by 18 days.

(21) Appl. No.: 18/408,908

(22) Filed: Jan. 10, 2024

(65) Prior Publication Data

US 2024/0141271 A1    May 2, 2024

Related U.S. Application Data

(63) Continuation of application No. 17/315,290, filed on May 8, 2021, now Pat. No. 11,879,118, which is a continuation-in-part of application No. 17/094,222, filed on Nov. 10, 2020, now Pat. No. 11,879,117.

(51) Int. Cl.
*C12M 1/12* (2006.01)
*C12M 1/00* (2006.01)

(52) U.S. Cl.
CPC ............ *C12M 23/04* (2013.01); *C12M 23/26* (2013.01); *C12M 23/34* (2013.01); *C12M 23/38* (2013.01); *C12M 37/04* (2013.01); *C12M 45/22* (2013.01)

(58) Field of Classification Search
CPC ...... C12M 23/04; C12M 23/26; C12M 23/34; C12M 23/38; C12M 37/04; C12M 45/22
USPC ....................................................... 435/288.3
See application file for complete search history.

(56) References Cited

U.S. PATENT DOCUMENTS

| | | | | |
|---|---|---|---|---|
| 4,054,490 | A * | 10/1977 | Vesterberg ............. | C12M 23/34 435/304.2 |
| 4,204,045 | A | 5/1980 | Kjellander et al. | |
| 4,271,270 | A * | 6/1981 | Lukacsek ............... | C12M 23/38 435/305.3 |
| 6,649,406 | B1 * | 11/2003 | Williams ............... | C12M 23/04 435/39 |
| 11,879,118 | B2 * | 1/2024 | Hyland .................. | C12M 23/22 |
| 2014/0196550 | A1* | 7/2014 | Chernomorsky ...... | C12M 23/12 73/864.91 |

FOREIGN PATENT DOCUMENTS

| | | |
|---|---|---|
| CN | 204065013 | 12/2004 |
| CN | 106591127 A | 4/2017 |
| EP | 0402888 A1 | 12/1990 |

* cited by examiner

*Primary Examiner* — Michael L Hobbs
*Assistant Examiner* — Lenora A Abel
(74) *Attorney, Agent, or Firm* — John L. Rogitz

(57) ABSTRACT

A gel tray for a bacterial transformation lab exercise has a plastic body with four parallel gel channels and four filling ports, one for each channel into which unmodified bacteria and heat-shocked bacteria can be injected by students along with appropriate reaction constituents to demonstrate transformation of the bacteria under visualization. A seal may be provided to seal the tops of the gel channels and a lid can cover the gel tray during incubation.

23 Claims, 7 Drawing Sheets

GEL TRAY FOR BACTERIA TRANSFORMATION LAB

FIELD

This application relates to gel trays for bacterial growth, including genetic transformation labs.

BACKGROUND

The present assignee's U.S. Pat. No. 9,835,587, incorporated herein by reference, discloses a commercially successful electrophoresis running tank assembly for use in the classroom to aid students in learning modern DNA assay techniques.

SUMMARY OF THE INVENTION

Present principles are directed to a plastic tray with plural channels to hold bacterial growth medium for the purpose of viewing bacterial growth or behavior. Current methods of growing bacteria are generally intended for professional laboratory personnel. The protocol and process are time consuming, cumbersome, and unreliable for high school education. Students need a system that allows them to reliably get the intended results while performing steps that mirror everyday biotech research and development.

One application is observing the results of bacterial transformation, the introduction of new behavior in bacteria through the introduction of foreign DNA. This behavior can include antibiotic resistance, fluorescence, or production of a desired protein. Introduction of antibiotic resistance into a previously antibiotic sensitive bacteria strain via DNA is a seminal discovery that forms an important foundation of biotechnology. The importance of bacterial transformation in the field of biotechnology makes it a key concept to be taught in high schools and colleges. Control of gene expression is also an important concept in biotechnology.

Accordingly, a gel tray assembly includes a gel tray body that defines a top surface. Plural gel channels are formed in the gel tray body parallel to each other, with at least first and second of the gel channels being separated from each other by a rib defining a top surface. Also, plural filling ports are provided, each having a fill end for receiving samples and a channel end communicating with an end of a respective one of the gel channels. Each filling port defines an axis from the respective fill end to the respective channel end. A flexible sheet is disposed on the top surface of the gel tray body and on the top surface of the rib and covering the gel channels and filling ports while preventing fluid communication between the gel channels.

In some examples an oblique angle is established between the axis of at least one of the filling ports and a longitudinal axis of its respective gel channel.

In example implementations the fill ends are elevated above the channel ends on the body.

If desired, at least one constituent can be in the gel channels to deter the growth of microbes during storage.

Respective gels may be disposed in the gel channels.

In example embodiments a lid covers the flexible sheet and the gel tray body. The gel tray body may be regarded as a first gel tray body and the lid defines a top surface comprising plural parallel ribs for receiving, between adjacent ribs, gel channels of a second gel tray body. The second gel tray body may be part of the assembly, disposed on the top surface of the lid.

In another aspect, a method includes adding gel to each of plural receptacles in a gel tray and preventing fluid communication between the receptacles regardless of an orientation of the gel tray.

In another aspect, a gel tray, e.g., for a bacteria transformation observation includes a plastic body with plural (e.g., from two to ten and in specific examples four) parallel gel channels into which unmodified bacteria and genetically modified bacteria can be added along with appropriate reaction constituents to demonstrate transformation of the bacteria under visualization. A seal is placed on top surfaces of the plastic body and gel channels to prevent fluid communication between the gel channels.

The details of the present application, both as to its structure and operation, can best be understood in reference to the accompanying drawings, in which like reference numerals refer to like parts, and in which:

DETAILED DESCRIPTION

Figure 1:
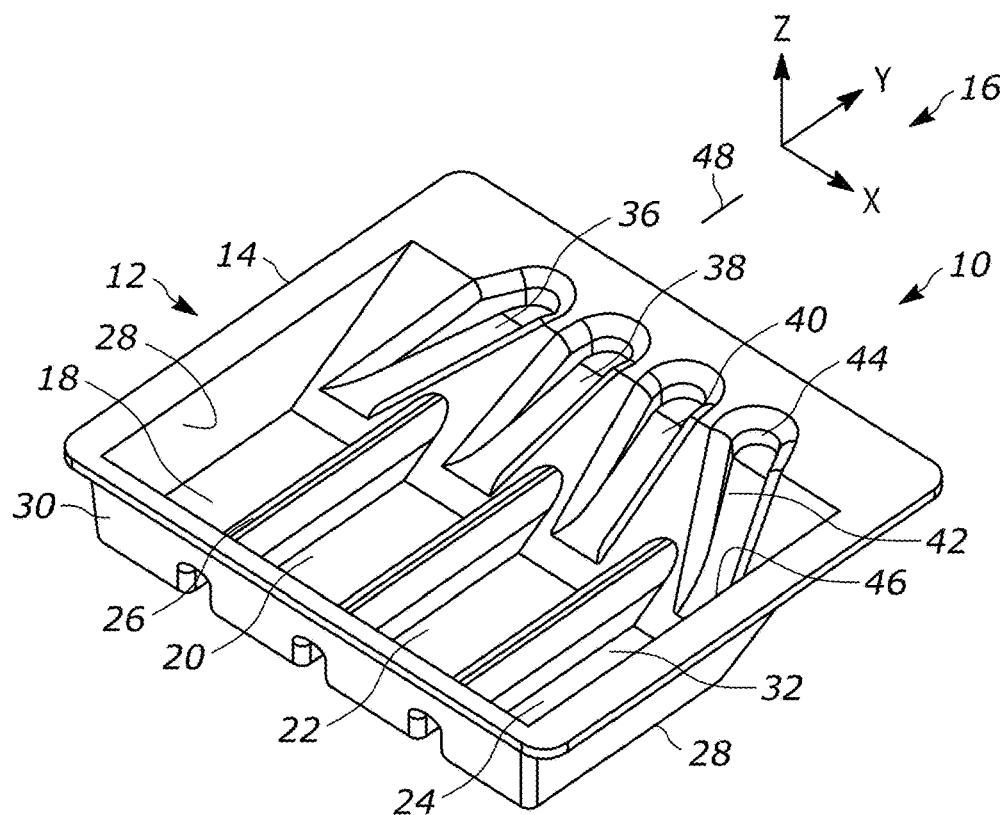
FIG. 1 is an isometric view of the gel tray when empty from a top perspective.
Figure 2:
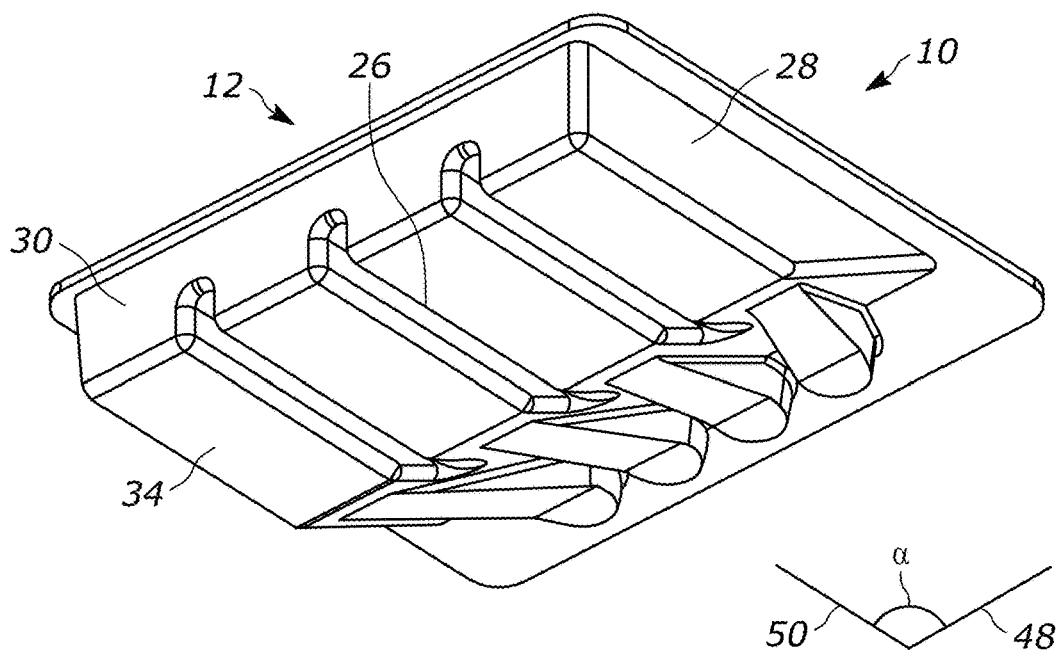
FIG. 2 is an isometric view of the gel tray when empty from a bottom perspective.

Referring initially to FIGS. 1 and 2, an assembly is shown, generally designated 10, which can be used for observing bacterial growth, is particularly, although not exclusively suited for academic use by students. The assembly 10 includes a plastic body 12 which in some embodiments may be transparent, with a generally parallelepiped-shaped periphery 14 in an x-y (horizontal) plane indicated by the axes 16 that is established when the body 12 is oriented as operationally intended on a viewing assembly as discussed further below. The body 12 may be a unitary piece of plastic formed by, e.g., injection molding.

In the example shown, first through fourth gel channels 18, 20, 22, 24 are formed in the body 12 parallel to each other, although in other embodiments a fewer or greater number of gel channels may be used, e.g., any integer number of gel channels from two on up. The gel channels are separated from each other by raised elongated ribs 26 that are parallel to the gel channels and that are elongated in the same dimension as the gel channels are elongated. The outer gel channels 18, 24 are thus bounded by respective vertical sidewalls 28 of the body 12 and on their sides opposite the sidewalls 28 by a respective rib 26, while the inner gel channels 20, 22 are bounded on both sides by ribs 26. The gel channels extend in length from a common end wall 30 to respective channel ends 32, and the bottom walls 34 of the gel channels 18-24 lie in the horizontal plane.

Extending upwardly (in the z-dimension) from the horizontal gel channels at oblique angles to the horizontal plane if desired, are first through fourth filling ports 36, 38, 40, 42, each having a respective fill end 44 that may have a semi-circular circumference if desired as shown. More generally, a filling port may be provided for each gel channel. The fill ends are configured for receiving constituent samples from a dispenser such as a micropipette or multi-channel pipette. Each filling port 36-42 extends from its fill end 44 to a respective channel end 46 that communicates with a respective channel end 32 of a respective one of the gel channels. The fill ends 44 thus may be elevated above the channel ends 46 of the fill ports on the body.

The respective channel ends 32, 46 of a respective gel channel/filling port pair are closely juxtaposed as shown such that constituent deposited in the fill end 44 of a filling port flows down the filling port under gravity through the channel ends 32, 46 and into the respective gel channel. In the example shown, each filling port is elongated from end 44 to end 46 and defines an axis there between with a component 48 in the horizontal plane. As best shown in FIG. 2, an oblique angle α can be established between the axis component 48 of at least one of the filling ports and a longitudinal axis 50 of its respective gel channel.

Figure 3:
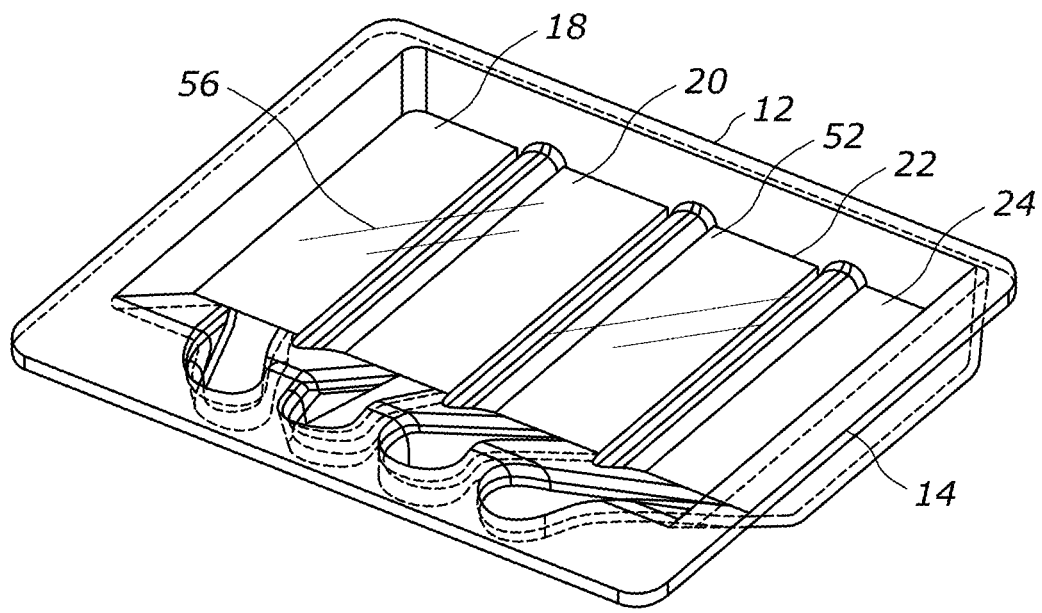
FIG. 3 is an isometric view of the gel tray when filled with gel and covered with film.

FIG. 3 illustrates that respective gels 52 may be disposed in the first through fourth gel channels 18-24 on the bottoms thereof. The gels 52 may contain a constituent to deter the growth of microbes during storage. In one example, the gels 52 are essentially growth media and may be composed of, e.g., lysogeny broth agar that contains chloramphenicol to deter the growth of wild bacteria, yeast, or other microbes during storage.

A protective plastic sheet 56, which may be transparent, may cover the interior of the body 12 as shown and may extend across the periphery 14 from all four sides (FIG. 3 illustrates the sheet 56 by means of shading lines.) The assembly shown in FIG. 3 may be vended to end users who can then add constituents to one or more of the gels 52 as discussed further below. Or the body 12 alone may be vended to end users who can fill the gel channels 18-24 with the gels 52.

It may now be appreciated that the gel tray assembly 10 may include four separate pools of growth media (gels), for example, one for a control and three for variations. The body 12 of the tray can be transparent (which include translucent) to allow light to pass through the bottom 34 and into the contents of the gel channels 18-24 tray.

Figure 4:
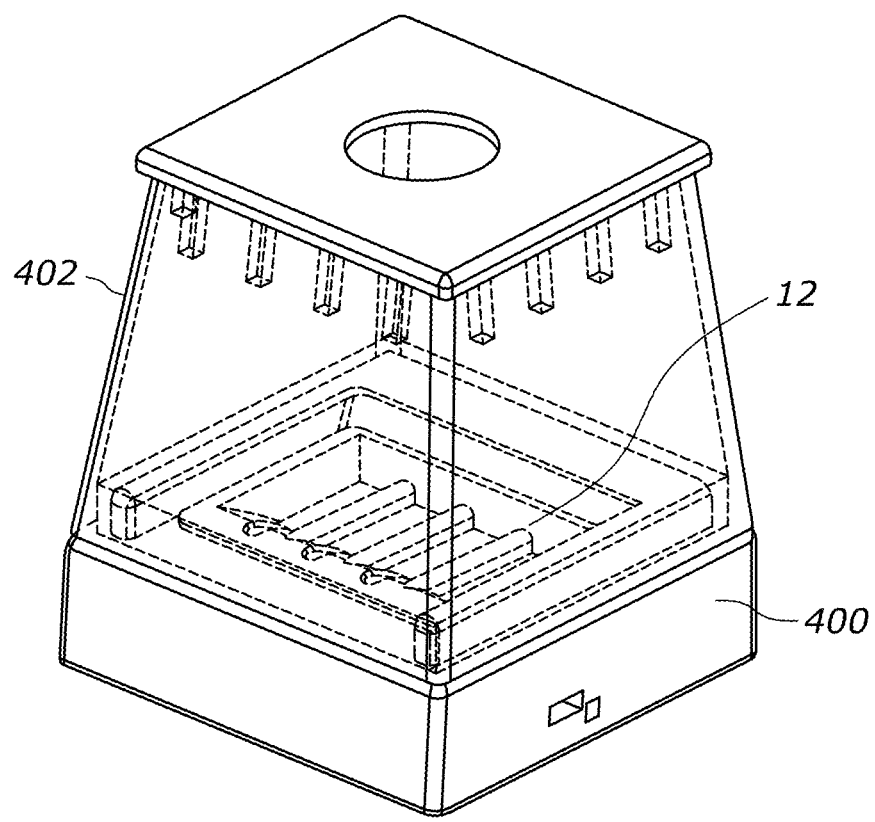
FIG. 4 is an isometric view of the gel tray in a viewer.
Figure 5:
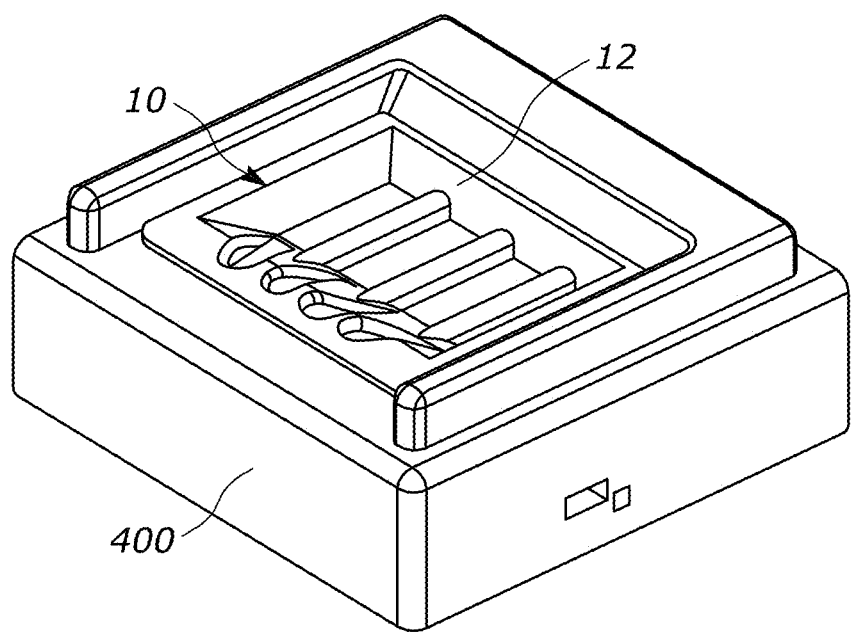
FIG. 5 is an isometric view of the gel tray on a viewer base.

FIGS. 4 and 5 illustrate that the body 12 of the gel tray is designed to fit onto a base 400 of a viewing assembly such as but not limited to that described in the referenced U.S. patent, to be covered by a hood 402 such as the hood described in the referenced U.S. patent, with the base 400 including lamps to illuminate the tray assembly 10 from below and photograph the tray assembly from above through an optical filter to detect and record presence of bacteria colonies and whether or not they exhibit fluorescence. The base 400 and hood 402 alternatively may be implemented by a simpler design apart from that referenced in the U.S. patent, marketed by the instant assignee under the trade name "The Winston™". The body 12 of the tray assembly 10 is designed to be easily filled, sterilized, and sealed to meet storage and shipping requirement, and to be easily unsealed by removing the sheet 56 to allow a student to introduce bacterial samples and subsequently resealed to allow for effective incubation of the experiment. The base 400 or other component may include heaters and/or coolers such as thermoelectric coolers to maintain temperature of constituents in the gel tray. Also, illumination may be from the sides or even top of the gel tray in addition to or in lieu of bottom illumination.

Unmodified bacteria host cells may be disposed in the first gel channel 18 by an end user. Such cells may be, in one example, a strain (BL21) of E. coli bacteria that already has resistance to chloramphenicol.

In one example implementation, unmodified bacteria and an antibiotic may be added to the second gel channel 20 by an end user. For example, ampicillin may be used to demonstrate that this antibiotic will kill bacteria that have not been transformed with an ampicillin resistance gene. Antibiotics other than ampicillin may be used.

Added to the third gel channel 22 may be genetically modified bacteria such as bacteria transformed with a plasmid (vector) through heat-shocking or another method. Prior to heat-shocking, bacteria may be made competent by the addition of a chemical, for example, calcium chloride. The plasmid (vector) may include genes for making fluorescent protein molecules like eGFP (enhanced Green Florescent Protein), which glows green under blue light when the bacteria make it. The plasmid may also include an ampicillin resistance gene. That way ampicillin can be used to kill all of the bacteria that do not take up the plasmid.

Genetically modified bacteria may be added to the fourth gel channel 24 by the end user along with an antibiotic and a chemical, e.g., IPTG, to induce expression of an exogenous constituent, as described above. A plasmid vector may be incorporated which can be a plasmid developed specifically for the purpose of a lab activity that gives the bacteria resistance to ampicillin and, when activated by IPTG, induces the bacteria to produce a protein that is fluorescent (e.g., eGFP).

Preferably, the samples added to all gel channels are spread evenly over the surface of the agar to maximize growth. In one embodiment, the tray may be sealed again with the sheet 56 and incubated. In another embodiment, the user will not seal the tray before incubating. The user will place only the below-described lid over the tray, on which the lid does not create a seal, and then incubate.

Figure 6:
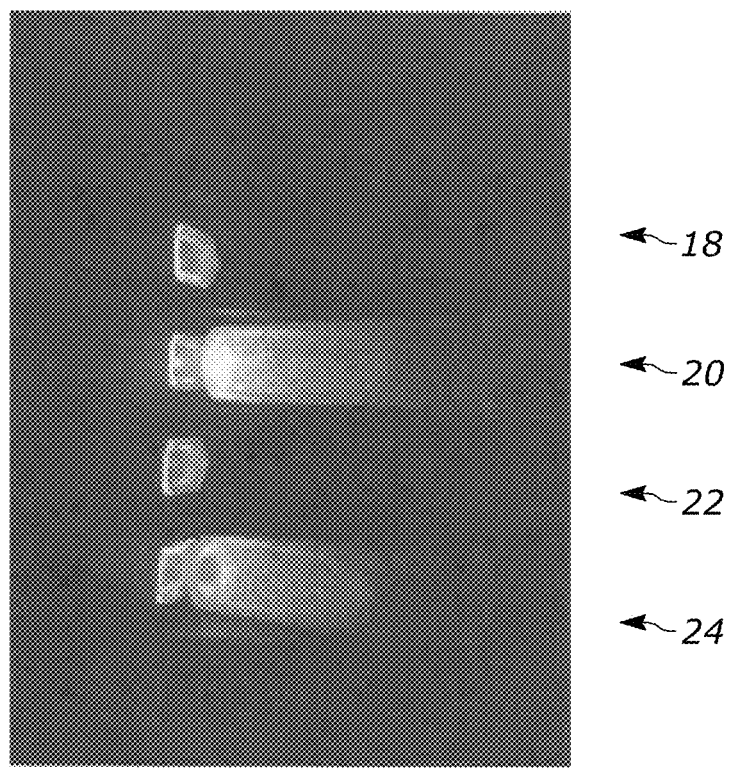
FIG. 6 shows colonies of genetically modified bacteria, transformed with a plasmid containing the gene for eGFP, growing in plastic tubes containing LB medium agar with chloramphenicol, ampicillin, and IPTG.
Figure 7:
FIG. 7 shows colonies of genetically modified bacteria, transformed with a plasmid containing the gene for eGFP, growing on a petri dish containing LB medium agar with chloramphenicol, ampicillin, and IPTG.

FIGS. 6 and 7 illustrate results.

Figure 8:
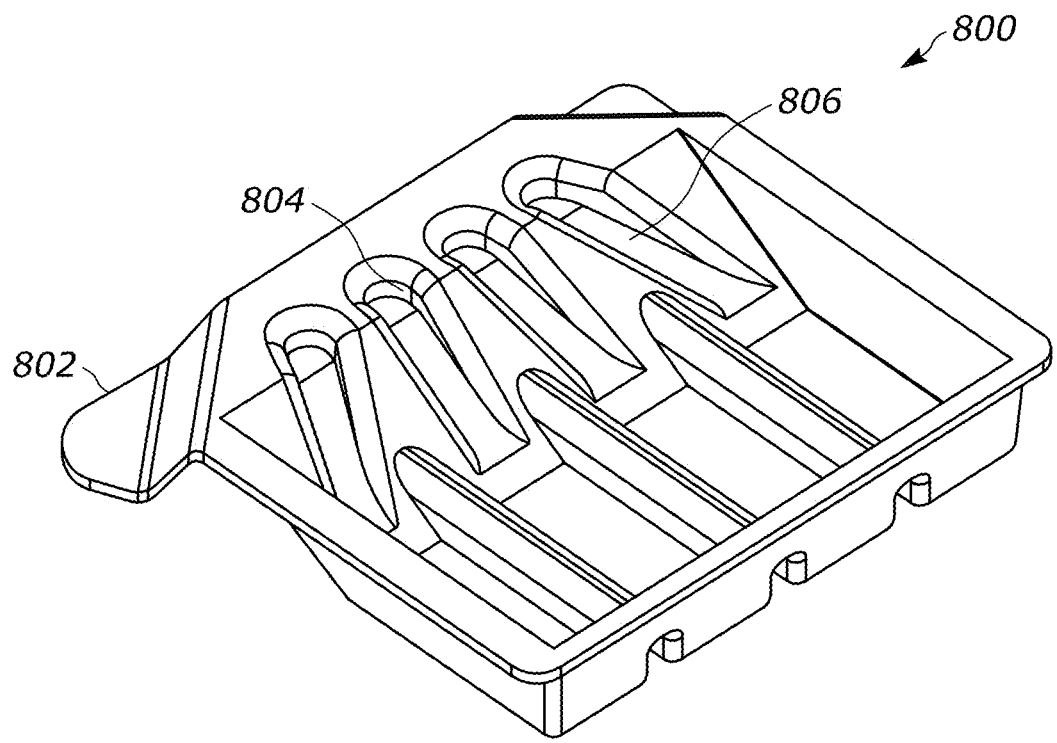
FIG. 8 is an isometric view of an alternate embodiment.

FIG. 8 illustrates a gel tray 800 that in all essential respects is identical in configuration and operation to the gel tray(s) shown previously with the following exception. The gel tray 800 in FIG. 8 includes tabbed corners 802 extending down and away from fill ends 804 of fill ports 806 to aid in removing the protective sheet discussed previously.

Figure 9:
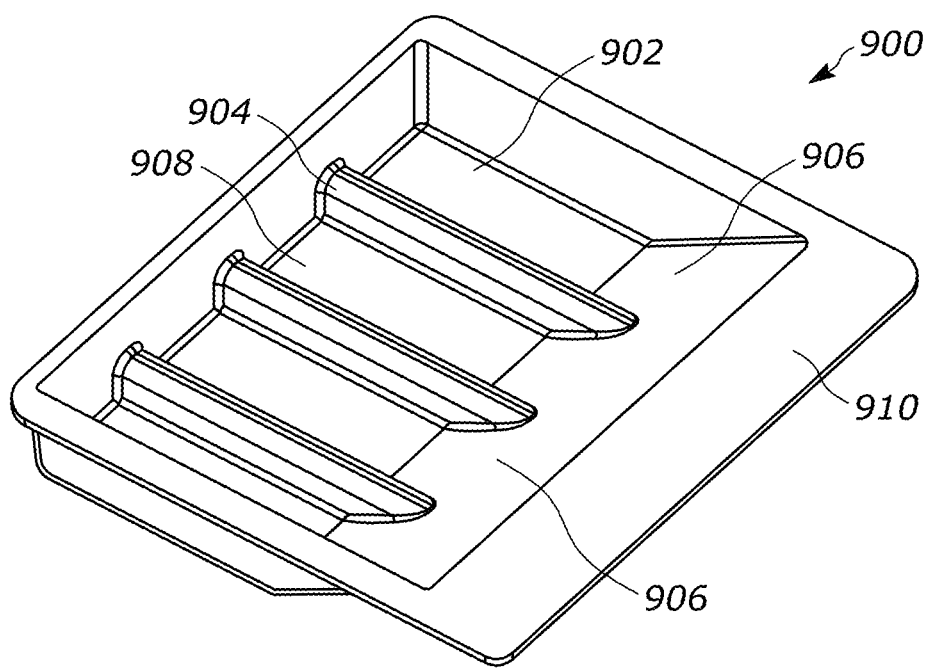
FIGS. 9 and 10 illustrate an alternate embodiment.
Figure 10:
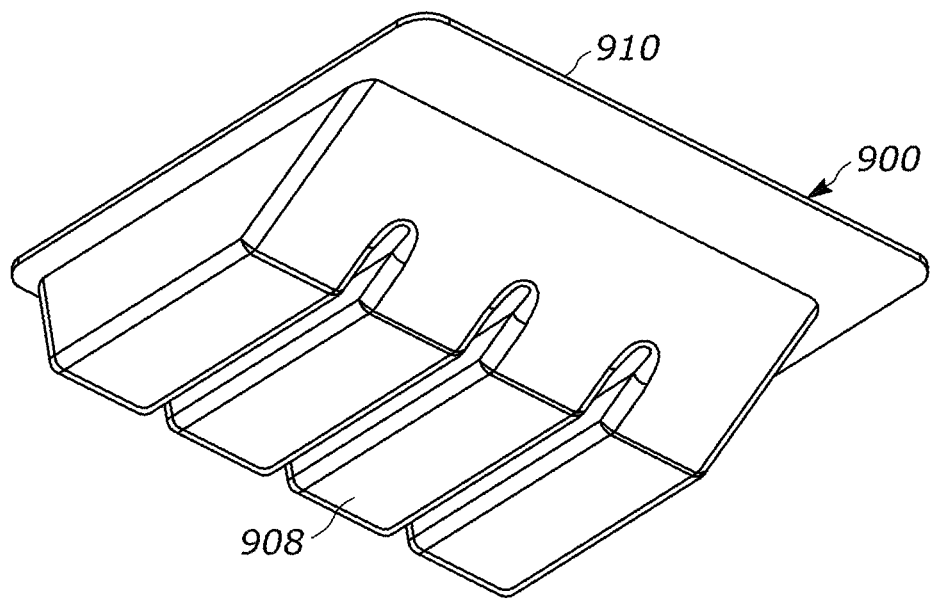

FIGS. 9 and 10 illustrate a gel tray 900 in all essential respects is identical in configuration and operation to the gel tray(s) shown previously with the following exception. The gel tray 900 in FIGS. 9 and 10 includes no separate fill ports, and includes plural (e.g., four) gel channels 902 separated by ribs 904 and terminating in a slanted wall 906 that extends upwardly and outwardly from the ends of bottoms 908 of the gel channels 902 at an oblique angle to the bottoms 908 to terminate in a flat edge flange 910 that is generally parallel to the bottoms 908 of the channels 902.

Figure 11:
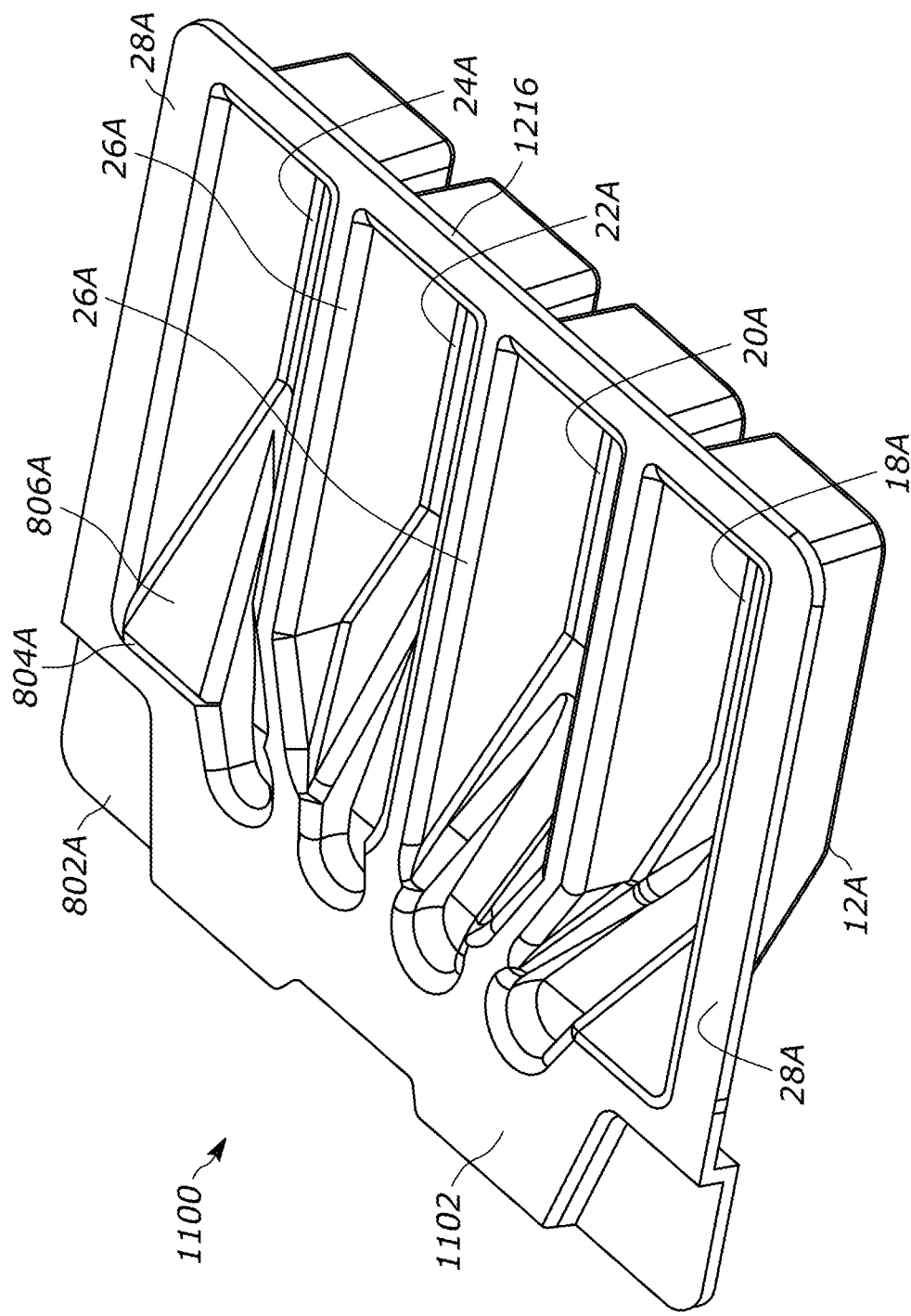
FIG. 11 is a perspective of yet another embodiment of the gel tray.
Figure 12:
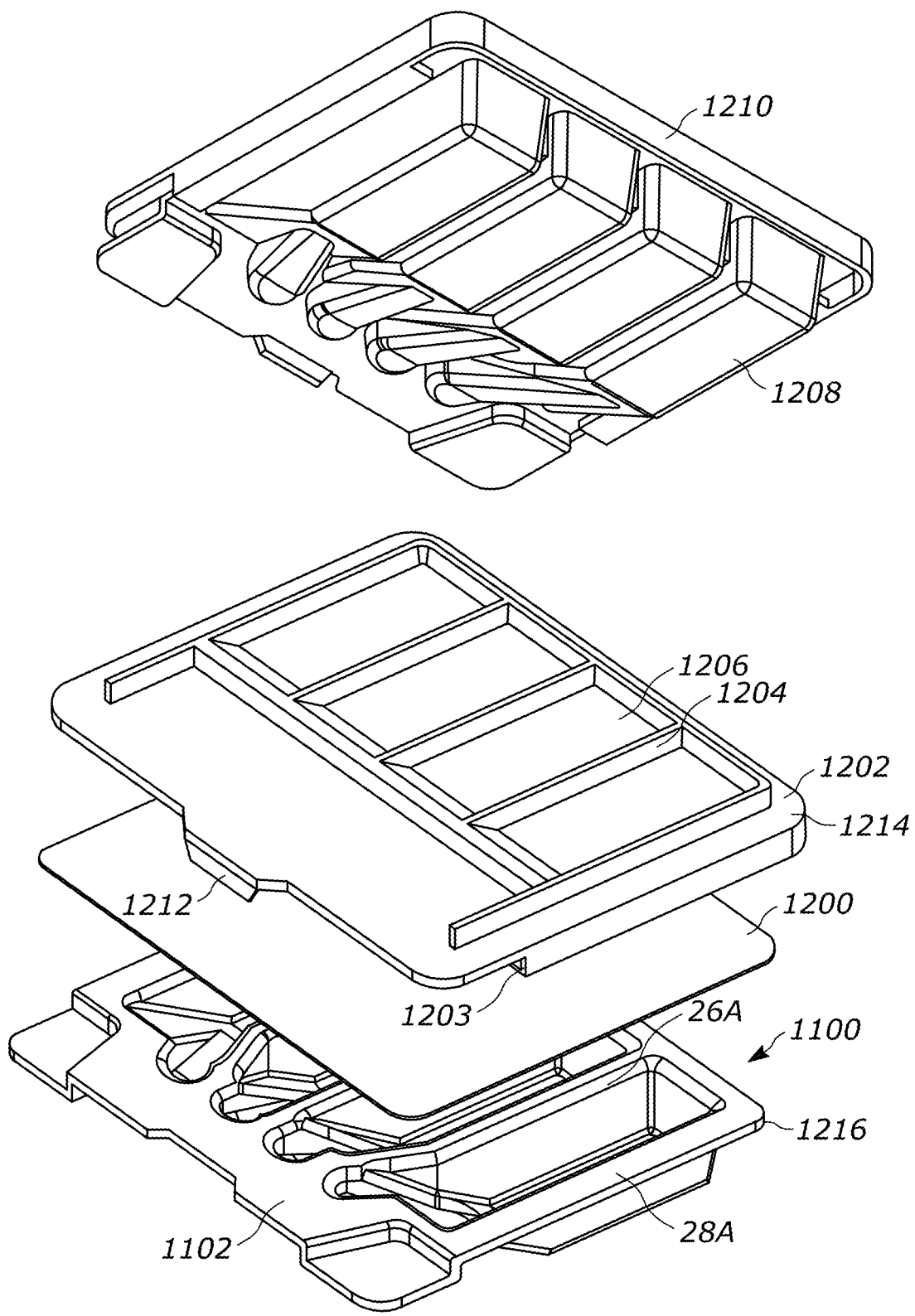
FIG. 12 is an exploded perspective view of the gel tray shown in FIG. 11, a seal, a lid, and a second gel tray that can stack on the lid.

FIGS. 11 and 12 illustrate a gel tray 1100 in all essential respects identical in configuration and operation to the gel tray(s) shown previously with the following exception. The gel tray 1100 in FIGS. 11 and 12 includes first through fourth gel channels 18A, 20A, 22A, 24A formed in a body 12A parallel to each other, although in other embodiments a fewer or greater number of gel channels may be used, e.g., any integer number of gel channels from two on up. The gel channels are separated from each other by raised elongated ribs 26A that are parallel to the gel channels and that are elongated in the same dimension as the gel channels are elongated. The outer gel channels 18A, 24A are thus bounded by respective vertical sidewalls 28A of the body 12A and on their sides opposite the sidewalls 28A by a respective rib 26A, while the inner gel channels 20A, 22A are bounded on both sides by ribs 26A.

In the example of FIGS. 11 and 12, the top edges of the ribs 26A are co-planar or substantially co-planar with the top edges of the sidewalls 28A. A flat top load flange 1102 extends from sidewall to sidewall along one end of the body 12A and the top surface of the flange 1102 likewise is co-planar or substantially co-planar with the top edges of the sidewalls 28A.

When a seal 1200 (FIG. 12) is placed over the gel channels 18A-24A, the seal 1200 contacts the top surfaces of the ribs 26A, sidewalls 28A, and flange 1102 to establish isolation of the gel channels from each other. This facilitates incubating material in the gel channels with the body 12A of the tray 1100 tray upside down as during manufacture and transport, preventing any condensation that might accumulate on the seal 1200 from cross contaminating among the gel channels. Thus, the gel tray may be sold with gel in the channels and the seal covering the gel. When it is desired to use the tray, the lid discussed further below is removed, the seal 1200 also is removed, and the bacteria and reagents added to the channels as described above. The lid may then be replaced onto the tray to cover the tray.

As was the case with the gel tray 800 in FIG. 8, the gel tray 1100 in FIGS. 11 and 12 may include tabbed corners 802A extending down and away from fill ends 804A of fill ports 806A to aid in removing the protective seal 1200 to facilitate removal of the seal 1200 from the body 12A. In an example embodiment, the seal 1200 may be a rectangular plastic sheet that is flexible and that is continuously solid between its rectangular edges to completely cover the gel channels and fill ports. The seal 1200 may be sized as shown to extend completely over the body 12 but not overlap past the periphery of the body 12.

As alluded to above, a rigid plastic lid 1202 also may be provided. The lid 1202 may be sized to fit over the gel tray 1100 with the seal 1200 sandwiched between the top edges of the gel tray and the bottom flat surface of the lid 1202. The lid may snappingly engage the body or fit over the edges of the body in an interference fit. In an example embodiment, the bottom left and right edges of the lid 1202 are formed with respective parallel U-shaped (in transverse cross-section) flanges 1203 that slidably engage respective sidewalls 28A of the gel tray, such that the lid 1202 can be advanced onto the sidewalls 28A, e.g., from the rear, and slid over the seal 1200 and gel tray 1100 until a 1212 (described further below) clears the front edge of the gel tray 1100, at which point the 1212 snaps down under material bias over the front edge of the gel tray.

The top surface of the lid 1202 may be formed with plural elongated raised ribs 1204 that establish a frame with cavities 1206 to receive the bottoms of respective gel channels 1208 of a second gel tray 1210, with the bottoms of the gel channels 1208 of the second gel tray 1210 closely fitting in respective cavities 1206 of the frame established by the ribs 1204 of the lid 1202. In this way, gel trays can be stacked one on top of the other.

The gel tray 1100 may be configured such that it can fit on the lid in only one direction. As discussed above, the lid 1202 may also include a tab 1212 that extends down in the opposite direction that the ribs 1206 extend up, to prevent accidental sliding out of the tray once the tab 1212 clears the front edge of the gel tray and snaps down over the front edge. Once the lid is completely slid on to the gel tray, a rear wall 1214 of the lid 1202 abuts the rear edge 1216 of the gel tray to trap the gel tray between the tab 1212 and rear wall 1214 of the lid. The seal can be removed from the gel tray and the lid can be re-engaged with the gel tray when the seal is removed.

While particular structures and techniques are herein shown and described in detail, it is to be understood that the subject matter which is encompassed by the present invention is limited only by the claims.

What is claimed is:

1. An apparatus comprising:
   a body;
   plural channels formed in the body;
   plural filling ports each having a fill end for receiving samples and a channel end communicating with an end of a respective one of the channels, each filling port defining an axis from the respective fill end to the respective channel end, bottom walls of the channels lying in a common plane, the filling ports extending upwardly from the channels at oblique angles to the common plane, the fill ends being elevated above the channel ends, each filling port being elongated from end to end; and
   a lid comprising left and right edges formed with respective flanges that slidably engage respective sidewalls of the body, such that the lid can be advanced onto the sidewalls and slid over the body.

2. The apparatus of claim 1, wherein the channels are separated from each other by raised elongated ribs that are parallel to the channels and that are elongated in a same dimension as the channels are elongated such that outer channels are bounded by respective vertical sidewalls of the body and on their sides opposite the sidewalls by a respective rib, while inner channels are bounded on both sides by ribs, the channels extending in length from a common end wall of the body to respective channel ends.

3. The apparatus of claim 1, wherein at least one fill end has a curvilinear circumference.

4. The apparatus of claim 1, comprising at least one constituent in the channels to deter the growth of microbes during storage.

5. The apparatus of claim 1, comprising respective gels in the channels.

6. The apparatus of claim 5, comprising unmodified bacteria host cells in a first one of the channels.

7. The apparatus of claim 5, comprising unmodified bacteria host cells and an antibiotic in a second one of the channels.

8. The apparatus of claim 5, comprising genetically modified bacteria host cells and a plasmid in a third one of the channels.

9. The apparatus of claim 5, comprising genetically modified bacteria host cells, an antibiotic, and a chemical to induce exogenous expression in a fourth one of the channels.

10. The apparatus of claim 1, wherein an oblique angle is established between the axis of at least one of the filling ports and a longitudinal axis of its respective channel.

11. A device comprising:
    a body;
    plural channels formed in the body; and plural filling ports each having a fill end for receiving samples and a channel end communicating with an end of a respective one of the channels, each filling port defining an axis from the respective fill end to the respective channel end, bottom walls of the channels lying in a common plane, a continuous oblique angle being established between the axis of at least one of the filling ports and a longitudinal axis of its respective channel, the fill ends being elevated above the channel ends, each filling port being elongated from end to end.

12. The device of claim 11, wherein the channels are separated from each other by raised elongated ribs that are parallel to the channels and that are elongated in a same dimension as the channels are elongated such that outer channels are bounded by respective vertical sidewalls of the body and on their sides opposite the sidewalls by a respective rib, while inner channels are bounded on both sides by ribs, the channels extending in length from a common end wall of the body to respective channel ends.

13. The device of claim 11, wherein at least one fill end has a curvilinear circumference.

14. The device of claim 11, comprising respective gels in the channels.

15. The device of claim 11, wherein the filling ports extend upwardly from the channels at oblique angles to the common plane.

16. The device of claim 11, comprising a lid slidably engaged with the body.

17. An apparatus, comprising:
a body;
plural channels formed in the body and configured for receiving gel;
plural filling ports each having a fill end for receiving samples and a channel end communicating with an end of a respective one of the channels; and
a lid slidably engaged with the body to cover the channels.

18. The apparatus of claim 17, wherein the lid is configured such that it can slide onto the body in only one direction.

19. The apparatus of claim 17, comprising a seal sandwiched between the lid and body.

20. An apparatus, comprising:
a body;
plural channels formed in the body and configured for receiving gel;
plural filling ports each having a fill end for receiving samples and a channel end communicating with an end of a respective one of the channels; and
a lid slidably engaged with the body to cover the channels, wherein the lid comprises left and right edges formed with respective flanges that slidably engage respective sidewalls of the body, such that the lid can be advanced onto the sidewalls and slid over the body until a tab of the lid clears a front edge of the body.

21. The apparatus of claim 20, wherein tab extends in an opposite direction to a direction in which the ribs of the lid extend to prevent the lid sliding off the body once the tab clears a front edge of the body.

22. The apparatus of claim 21, wherein the lid is completely slid on to the body and a rear wall of the lid abuts a rear edge of the body to trap the body between the tab and rear wall of the lid.

23. An apparatus, comprising:
a body;
plural channels formed in the body and configured for receiving gel;
plural filling ports each having a fill end for receiving samples and a channel end communicating with an end of a respective one of the channels; and
a lid slidably engaged with the body to cover the channels, wherein the body is a first body and a top surface of the lid is formed with plural elongated raised ribs that establish cavities to receive bottoms of respective gel channels of a second body.

* * * * *